United States Patent
Hirson et al.

(10) Patent No.: US 9,273,570 B2
(45) Date of Patent: Mar. 1, 2016

(54) METHODS FOR POWER GENERATION FROM $H_2O$, $CO_2$, $O_2$ AND A CARBON FEED STOCK

(71) Applicant: POWERDYNE, INC., Newport Beach, CA (US)

(72) Inventors: Geoffrey Hirson, Newport Beach, CA (US); Gus F. Shouse, Newport Beach, CA (US)

(73) Assignee: Powerdyne, Inc., Newport Beach, CA (US)

( * ) Notice: Subject to any disclaimer, the term of this patent is extended or adjusted under 35 U.S.C. 154(b) by 0 days.

(21) Appl. No.: 14/426,093

(22) PCT Filed: Sep. 5, 2013

(86) PCT No.: PCT/US2013/058305
§ 371 (c)(1),
(2) Date: Mar. 4, 2015

(87) PCT Pub. No.: WO2014/039706
PCT Pub. Date: Mar. 13, 2014

(65) Prior Publication Data
US 2015/0275705 A1    Oct. 1, 2015

Related U.S. Application Data

(60) Provisional application No. 61/697,148, filed on Sep. 5, 2012.

(51) Int. Cl.
*F23J 15/00*  (2006.01)
*F01K 25/06*  (2006.01)
(Continued)

(52) U.S. Cl.
CPC ............ *F01K 25/06* (2013.01); *B01D 21/0009* (2013.01); *B01D 21/01* (2013.01);
(Continued)

(58) Field of Classification Search
CPC ............ B23K 9/00; B23K 10/00; F23J 15/00; F23B 10/02
See application file for complete search history.

(56) References Cited

U.S. PATENT DOCUMENTS

| 1,746,464 A   | 2/1930 | Fischer et al. |
| 3,979,205 A * | 9/1976 | Wanzenberg ............. C22B 1/00 423/22 |

(Continued)

FOREIGN PATENT DOCUMENTS

| CA | 2379892 A1 | 2/2001 |
| CN | 1268550 A  | 10/2000 |

(Continued)

OTHER PUBLICATIONS

International Search Report and Written Opinion dated Feb. 24, 2015 for International Application No. PCT/US2014/069342.

(Continued)

*Primary Examiner* — Thomas Denion
*Assistant Examiner* — Shafiq Mian
(74) *Attorney, Agent, or Firm* — Pepper Hamilton LLP

(57) ABSTRACT

In a first processing chamber, a feedstock may be combined with plasma from three plasma torches to form a first fluid mixture. Each torch may have a working gas including water vapor, oxygen, and carbon dioxide. The first fluid mixture may be cooled and may contact a first heat exchange device. Water in the first heat exchange device may be converted to steam to generate electric power. The output fluid from the first heat exchange device may be separated into one or more components. A syngas may be derived from the one or more components and have a ratio of carbon monoxide to hydrogen of about 1:2. The syngas may be heated in a second processing chamber and then cooled to form a second admixture. The second admixture may contact a second heat exchange device that may make steam to power a second electrical generator.

20 Claims, 3 Drawing Sheets

(51) Int. Cl.

| | | |
|---|---|---|
| *B01J 12/00* | (2006.01) | |
| *C01B 3/04* | (2006.01) | |
| *B01D 21/00* | (2006.01) | |
| *B01D 21/01* | (2006.01) | |
| *B09B 3/00* | (2006.01) | |
| *H05H 1/42* | (2006.01) | |
| *H05H 1/44* | (2006.01) | |
| *C01B 3/12* | (2006.01) | |
| *C07C 1/04* | (2006.01) | |
| *C10G 2/00* | (2006.01) | |
| *B01J 19/08* | (2006.01) | |
| *C01B 3/02* | (2006.01) | |
| *C10L 1/06* | (2006.01) | |
| *C10L 1/08* | (2006.01) | |
| *H05H 1/34* | (2006.01) | |
| *F02C 1/05* | (2006.01) | |

(52) U.S. Cl.
CPC ............ *B01J 12/002* (2013.01); *B01J 19/088* (2013.01); *B09B 3/005* (2013.01); *C01B 3/02* (2013.01); *C01B 3/042* (2013.01); *C01B 3/12* (2013.01); *C07C 1/04* (2013.01); *C10G 2/32* (2013.01); *C10L 1/06* (2013.01); *C10L 1/08* (2013.01); *F02C 1/05* (2013.01); *H05H 1/34* (2013.01); *H05H 1/42* (2013.01); *H05H 1/44* (2013.01); *B01J 2219/0809* (2013.01); *B01J 2219/0815* (2013.01); *B01J 2219/0875* (2013.01); *B01J 2219/0877* (2013.01); *B01J 2219/0898* (2013.01); *C01B 2203/062* (2013.01); *C01B 2203/0861* (2013.01); *C10L 2200/043* (2013.01); *C10L 2200/0415* (2013.01); *C10L 2200/0423* (2013.01); *C10L 2200/0446* (2013.01); *C10L 2290/38* (2013.01); *C10L 2290/42* (2013.01); *Y02E 60/364* (2013.01)

(56) References Cited

U.S. PATENT DOCUMENTS

| | | | |
|---|---|---|---|
| 4,466,807 A | 8/1984 | Santen et al. | |
| 4,508,040 A | 4/1985 | Santen et al. | |
| 4,591,428 A | 5/1986 | Pronk | |
| 4,770,109 A * | 9/1988 | Schlienger | C03B 5/005 |
| | | | 110/247 |
| 4,831,944 A | 5/1989 | Durand et al. | |
| 4,845,334 A | 7/1989 | Stocks et al. | |
| 4,898,748 A | 2/1990 | Kruger, Jr. | |
| 5,046,144 A | 9/1991 | Jensen | |
| 5,107,517 A | 4/1992 | Lauren | |
| 5,136,137 A * | 8/1992 | Schlienger | C03B 5/005 |
| | | | 110/246 |
| 5,138,959 A | 8/1992 | Kulkarni | |
| 5,288,969 A | 2/1994 | Wong et al. | |
| 5,301,620 A | 4/1994 | Nagel et al. | |
| 5,319,176 A | 6/1994 | Alvi et al. | |
| 5,493,578 A | 2/1996 | Fukusaki et al. | |
| 5,534,659 A | 7/1996 | Springer et al. | |
| 5,541,386 A | 7/1996 | Alvi et al. | |
| 5,544,597 A | 8/1996 | Camacho | |
| 5,611,947 A * | 3/1997 | Vavruska | H05H 1/24 |
| | | | 110/238 |
| 5,634,414 A | 6/1997 | Camacho | |
| 5,673,635 A | 10/1997 | Fowler | |
| 5,725,616 A | 3/1998 | Lynum et al. | |
| 5,798,496 A | 8/1998 | Eckhoff et al. | |
| 5,935,293 A | 8/1999 | Detering et al. | |
| 5,958,264 A | 9/1999 | Tsantrizos et al. | |
| 6,127,645 A | 10/2000 | Titus et al. | |
| 6,153,852 A * | 11/2000 | Blutke | F23G 5/085 |
| | | | 110/346 |
| 6,173,002 B1 | 1/2001 | Robert | |
| 6,187,226 B1 | 2/2001 | Detering et al. | |
| 6,215,678 B1 | 4/2001 | Titus et al. | |
| 6,289,851 B1 | 9/2001 | Rabovitser et al. | |
| 6,355,904 B1 | 3/2002 | Batdorf et al. | |
| 6,372,156 B1 * | 4/2002 | Kong | B01J 12/002 |
| | | | 252/373 |
| 6,375,832 B1 | 4/2002 | Eliasson et al. | |
| 6,505,567 B1 | 1/2003 | Anderson et al. | |
| 6,524,538 B2 | 2/2003 | Barankova et al. | |
| 6,552,295 B2 | 4/2003 | Markunas et al. | |
| 6,810,821 B2 | 11/2004 | Chan | |
| 6,821,500 B2 | 11/2004 | Fincke et al. | |
| 6,874,434 B1 | 4/2005 | Bigelow et al. | |
| 6,971,323 B2 | 12/2005 | Capote et al. | |
| 6,976,362 B2 * | 12/2005 | Sheppard | C01B 3/32 |
| | | | 60/39.12 |
| 6,987,792 B2 | 1/2006 | Do et al. | |
| 7,070,634 B1 * | 7/2006 | Wang | B01J 19/088 |
| | | | 422/168 |
| 7,097,675 B2 | 8/2006 | Detering et al. | |
| 7,279,655 B2 * | 10/2007 | Blutke | C01B 3/342 |
| | | | 110/211 |
| 7,335,320 B2 | 2/2008 | Kingdig et al. | |
| 7,384,619 B2 | 6/2008 | Bar-Gadda | |
| 7,576,296 B2 | 8/2009 | Fincke et al. | |
| 7,622,693 B2 | 11/2009 | Foret | |
| 7,674,443 B1 | 3/2010 | Davis | |
| 7,832,344 B2 | 11/2010 | Capote et al. | |
| 7,845,411 B2 | 12/2010 | Vinegar et al. | |
| 7,981,371 B2 | 7/2011 | Meillot et al. | |
| 8,129,654 B2 | 3/2012 | Lee et al. | |
| 8,168,128 B2 | 5/2012 | Seely et al. | |
| 8,199,790 B2 | 6/2012 | Vera | |
| 8,216,433 B2 | 7/2012 | Yonesu | |
| 8,252,244 B2 | 8/2012 | Capote et al. | |
| 8,268,094 B2 * | 9/2012 | Zurecki | H05H 1/48 |
| | | | 148/217 |
| 8,277,631 B2 | 10/2012 | Eastman et al. | |
| 8,303,916 B2 | 11/2012 | Collins et al. | |
| 8,324,523 B2 | 12/2012 | Foret | |
| 8,357,873 B2 | 1/2013 | Foret | |
| 8,367,005 B2 | 2/2013 | Ikeda et al. | |
| 8,475,551 B2 | 7/2013 | Tsangaris et al. | |
| 8,518,162 B2 | 8/2013 | Smith et al. | |
| 8,519,354 B2 | 8/2013 | Charipar et al. | |
| 2002/0000085 A1 | 1/2002 | Hall et al. | |
| 2002/0040889 A1 | 4/2002 | Markunas et al. | |
| 2002/0151604 A1 | 10/2002 | Detering et al. | |
| 2003/0029796 A1 | 2/2003 | Maekawa | |
| 2003/0065042 A1 | 4/2003 | Shaw | |
| 2003/0209174 A1 | 11/2003 | Chan | |
| 2004/0134517 A1 | 7/2004 | Clark | |
| 2006/0060464 A1 | 3/2006 | Chang | |
| 2006/0112639 A1 | 6/2006 | Nick et al. | |
| 2006/0201157 A1 | 9/2006 | Villalobos | |
| 2006/0233699 A1 | 10/2006 | Mills | |
| 2007/0017228 A1 | 1/2007 | Surma | |
| 2007/0186474 A1 | 8/2007 | Rabovitser et al. | |
| 2007/0253874 A1 | 11/2007 | Foret | |
| 2007/0266633 A1 | 11/2007 | Tsangaris et al. | |
| 2007/0267289 A1 | 11/2007 | Jabs et al. | |
| 2007/0272131 A1 | 11/2007 | Carabin et al. | |
| 2008/0041829 A1 | 2/2008 | Blutke et al. | |
| 2008/0083701 A1 | 4/2008 | Shao et al. | |
| 2008/0147241 A1 | 6/2008 | Tsangaris et al. | |
| 2008/0184621 A1 | 8/2008 | Clark | |
| 2008/0202028 A1 | 8/2008 | Tsangaris et al. | |
| 2008/0209807 A1 | 9/2008 | Tsangaris et al. | |
| 2008/0222956 A1 | 9/2008 | Tsangaris et al. | |
| 2008/0223047 A1 | 9/2008 | Oliver | |
| 2008/0277265 A1 | 11/2008 | Tsangaris et al. | |
| 2008/0283153 A1 | 11/2008 | Zurecki et al. | |
| 2008/0283411 A1 | 11/2008 | Eastman et al. | |
| 2008/0290322 A1 | 11/2008 | Hederer et al. | |
| 2009/0038958 A1 | 2/2009 | Coyle et al. | |
| 2009/0133407 A1 | 5/2009 | Sawyer | |
| 2009/0188127 A1 | 7/2009 | Gorbell et al. | |
| 2009/0307975 A1 | 12/2009 | Wolf | |

(56) References Cited

U.S. PATENT DOCUMENTS

| | | |
|---|---|---|
| 2010/0050654 A1 | 3/2010 | Chiu et al. |
| 2010/0065781 A1 | 3/2010 | Brothier |
| 2010/0167139 A1 | 7/2010 | Gattis et al. |
| 2010/0229522 A1 | 9/2010 | Kingzett |
| 2010/0298449 A1 | 11/2010 | Rojey |
| 2011/0067376 A1 | 3/2011 | Tompkins et al. |
| 2011/0162958 A1 | 7/2011 | Cho et al. |
| 2011/0212012 A1 | 9/2011 | McAlister |
| 2011/0265698 A1 | 11/2011 | Hirson et al. |
| 2011/0286893 A1 | 11/2011 | Zimmerman et al. |
| 2012/0000115 A1 | 1/2012 | Shastri |
| 2012/0070347 A1 | 3/2012 | Bacon et al. |
| 2012/0090985 A1 | 4/2012 | Rabinovich et al. |
| 2012/0114877 A1 | 5/2012 | Lee |
| 2012/0121468 A1 | 5/2012 | Tsangaris et al. |
| 2012/0291436 A1 | 11/2012 | Hirson et al. |
| 2013/0200624 A1 | 8/2013 | Hirson et al. |
| 2013/0300121 A1 | 11/2013 | Ali et al. |

FOREIGN PATENT DOCUMENTS

| | | |
|---|---|---|
| CN | 1810938 A | 8/2006 |
| EP | 1270508 A1 | 1/2003 |
| GB | 573982 | 12/1945 |
| WO | WO 2005/005009 A2 | 1/2005 |
| WO | WO 2008/130260 A1 | 10/2008 |
| WO | WO 2009/156761 A2 | 12/2009 |
| WO | WO 2010/056462 A1 | 5/2010 |
| WO | WO 2011/091327 A1 | 7/2011 |
| WO | WO 2011/140080 A2 | 11/2011 |
| WO | WO 2012/039751 A2 | 3/2012 |
| WO | WO 2012/064936 A1 | 5/2012 |
| WO | WO 2012/077198 A1 | 6/2012 |
| WO | WO 2012/158797 A1 | 11/2012 |
| WO | WO 2012/177666 A1 | 12/2012 |

OTHER PUBLICATIONS

"C-17 flight uses synthetic fuel blend," (Oct. 25, 2007), Wright-Patterson Air Force Base, Retrieved Feb. 7, 2008, http://www.wpafb.af.mil/news/story.asp?id=123073170.

Fairley, Peter, "Growing Biofuels," (Nov. 23, 2005), MIT Technology Review, http://www.technologyreview.com/news/404941/growing-biofuels/.

"Governor Rendell leads with innovative solution to help address PA energy needs," State of Pennsylvania. Archived from original on Dec. 11, 2008, http://web.archive.org/web/20081211180710/http:/www.state.pa.us/papower/cwp/view.asp?Q=446127&A=11.

Jamieson et al., "Keeping the Options Open", *Petroleum Economist*, Retrieved LNG 2012.

Krauss, Clifford, "South African Company to Build U.S. Plant to Convert Gas to Liquid Fuels," (Dec. 3, 2012), *New York Times*, http://www.nytimes.com/2012/12/04/business/energy-environment/sasol-plans-first-gas-to-liquids-plant-in-us.html?_r=1.

Lane, Jim, "Little Big Tech: Can Fischer-Tropsch technology work at smaller scale?" (Nov. 20, 2012), *Biofuels Digest*, http://www.biofuelsdigest.com/bdigest/2012/11/20/little-big-tech-can-fischer-tropsch-technology-work-at-smaller-scale/.

"PetroSA Wins Innovation Award," SouthAfrica.info, (Oct. 10, 2008), Retrieved Dec. 18, 2012, http://www.southafrica.info/business/trends/innovations/petrosa-101008.htm.

"PetroSA technology ready for next stage," Businessday.co.za, (May 10, 2011) Retrieved Jun. 5, 2013, http://www.bdlive.co.za/articles/2011/05/10/petrosa-technology-ready-for-next-stage.

Pitt, Anthea, "Linc gears up for Chinchilla GTL," (Nov. 28, 2012), Upstreamonline.com, http://www.upstreamonline.com/live/article1149671.ece?print=preview.

"Schweitzer wants to convert Otter Creek coal into liquid fuel," (Aug. 2, 2005), *Billings Gazette*, Archived from original on Jan. 1, 2009.

Smedley, Mark, "Small GTL's Market Reach as Great as Opec's, UK Firm Says," *World Gas Intelligence*, Retrieved Dec. 19, 2012, http://www.oxfordcatalysts.com/press/egs/world_gas_intelligence_1212194.pdf.

Steynberg et al., "Clean Coal Conversion Options Using Fischer-Tropsch Technology," (2003), Fuel Chemistry Division Preprints, 48(1); 459-461.

"UPM-Kymmene says to establish beachhead in biodesel market," NewsRoom Finland. Archived from original on Mar. 17, 2007, http://web.archive.org/web/20070317104947/http:/newsroom.finland.fi/stt/showarticle.asp?intNWSAID=14179&group=Business.

International Search Report and Written Opinion dated Jul. 28, 2014 for International Application No. PCT/US2014/024606.

International Search Report and Written Opinion dated Jan. 17, 2014 for International Application No. PCT/US2013/058287.

International Search Report and Written Opinion dated Feb. 7, 2014 for International Application No. PCT/US2013/058301.

International Search Report and Written Opinion dated Dec. 12, 2013 for International Application No. PCT/US2013/058305.

International Search Report and Written Opinion dated Feb. 7, 2014 for International Application No. PCT/US2013/058315.

International Search Report and Written Opinion dated Feb. 7, 2014 for International Application No. PCT/US2013/058326.

International Search Report and Written Opinion dated Jan. 22, 2014 for International Application No. PCT/US2013/058331.

International Search Report and Written Opinion dated Jan. 16, 2014 for International Application No. PCT/US2013/058335.

Plasco Group, "How is Plasco Different?," http://www.plascoenergygroup.com/our-solution/how-is-plasco-different/, retrieved from web Jul. 5, 2011.

Schuey et al., "LLW Processing and Operational Experience Using a Plasma ARC Centrifugal Treatment (PACT) System," *WM'06 Conference*, Feb. 26-Mar. 2, 2006, Tucson, AZ.

Urashima et al., "Removal of Volatile Organic Compounds from Air Streams and Industrial Flue Gases by Non-Thermal Plasma Technology," *IEEE Transactions on Dielectrics and Electrical Insulation*, Oct. 2000, 7(5):602-614.

* cited by examiner

US 9,273,570 B2

METHODS FOR POWER GENERATION FROM $H_2O$, $CO_2$, $O_2$ AND A CARBON FEED STOCK

CLAIM OF PRIORITY

This application is a national phase application under 35 U.S.C. 371 of International Application No. PCT/US2013/058305, entitled "Methods of Power Generation from $H_2O$, $CO_2$, $O_2$ and a Carbon Feed Stock," and filed Sep. 5, 2013, which claims the benefit of and priority to U.S. Provisional Patent Application No. 61/697,148, entitled "Methods for Generating Fuel Materials and Power, and Sequestering Toxins Using Plasma Sources," which was filed on Sep. 5, 2012. The aforementioned applications are incorporated by reference herein in their entireties and for all purposes.

BACKGROUND

Fuel materials may take on a variety of forms, from simple gasses such as hydrogen to complex mixtures including aviation fuels. Due to their wide range of chemical compositions, chemical fuels may be generated through a variety of processes and may require facilities dedicated to synthesizing only a small number of possible fuel types. Such facilities may be optimized to generate only the fuels to which they are dedicated. Additionally, each facility may require a specific set of feed-stocks or precursor materials for fuel synthesis.

Typically, carbon-based fuels rely on thermal methods for their synthesis. Such methods may include pyrolysis, cracking, and endothermic synthesis steps. Such processes may generate excessive heat as a by-product of their synthetic methods. Further, such thermal chemistry-based synthetic methods may not be efficient even for an optimized facility.

It is therefore desirable to develop high efficiency methods for generating a variety of gaseous and/or liquid fuels from a limited number of readily available feed stocks.

SUMMARY

In an embodiment, a method of producing electrical power may include providing a first processing chamber, providing a first working fluid, exposing the first working fluid to a first high voltage electric field to produce a first fluid plasma, in which the first fluid plasma may be contained in the first processing chamber, providing a second working fluid, exposing the second working fluid to a second high voltage electric field to produce a second fluid plasma, in which the second fluid plasma may be contained in the first processing chamber, providing a third working fluid, exposing the third working fluid to a third high voltage electric field to produce a third fluid plasma, in which the third fluid plasma may be contained in the first processing chamber, providing a carbon-based feed-stock, contacting the carbon-based feed-stock with the third fluid plasma, the second fluid plasma, and the first fluid plasma to form a first fluid mixture within the first processing chamber, adding a coolant to the first fluid mixture, thereby forming an admixed first fluid mixture, contacting the admixed first fluid mixture with a first heat exchange device to form a second fluid mixture and to heat a first heat exchange material, transporting the heated first heat exchange material to a first electric turbine to generate a first supply of electric power, separating the components of the second fluid mixture and storing at least one of the components, combining one or more of the components of the second fluid mixture thereby forming a syngas, heating the syngas within a second processing chamber to form a heated third fluid mixture, adding a coolant to the third fluid mixture, thereby forming an admixed third fluid mixture, contacting the heated admixed third fluid mixture with a second heat exchange device to form an effluent mixture and to heat a second heat exchange material, contacting the heated second heat exchange material with a second electric turbine to generate a second supply of electric power, and contacting the effluent mixture to a wet scrubber.

DETAILED DESCRIPTION

Figure 1A:
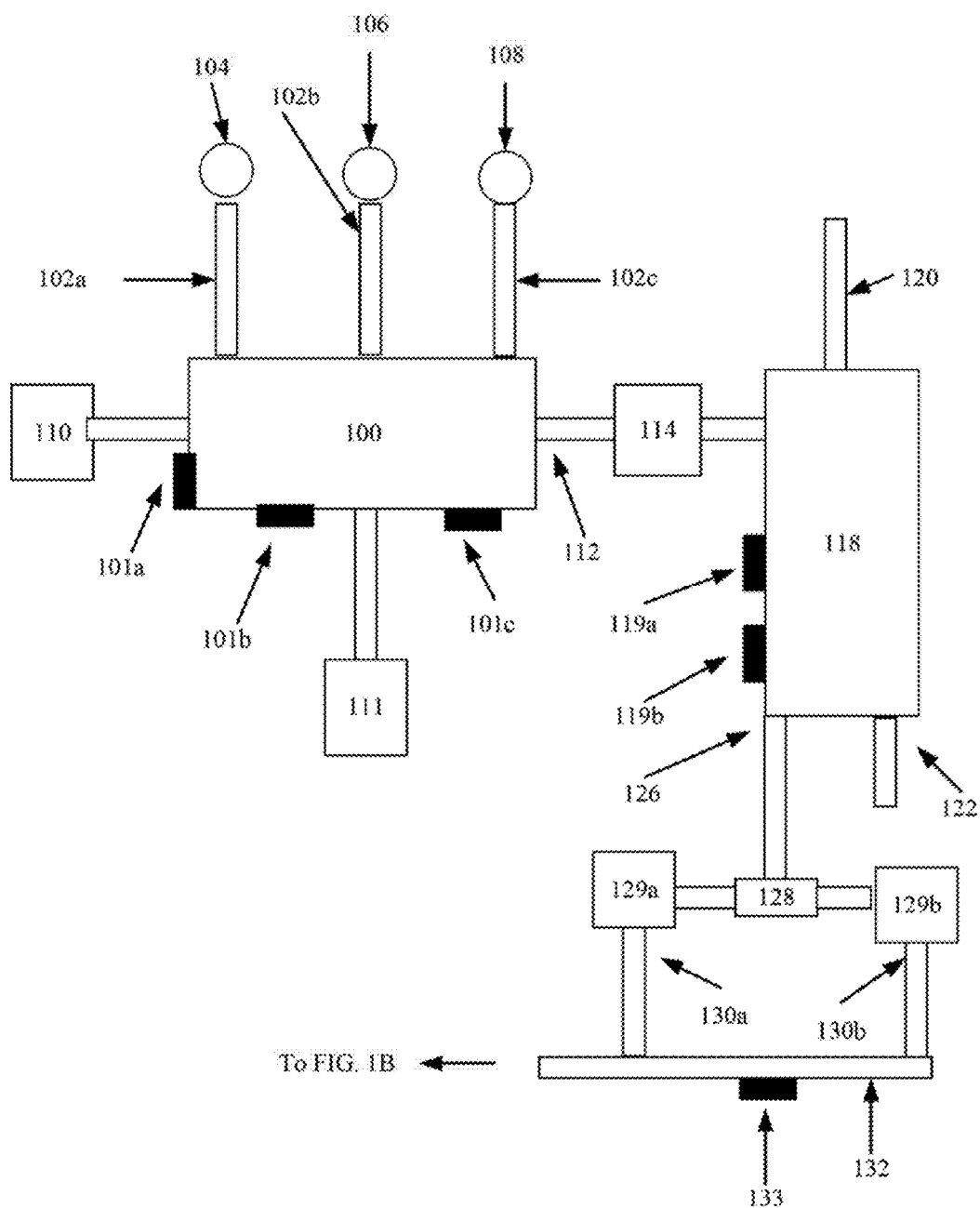
FIGS. 1A and 1B illustrate an embodiment of a system to implement a method for generating electric power from at least one plasma source and a carbon feedstock in accordance with the present disclosure.
Figure 1B:
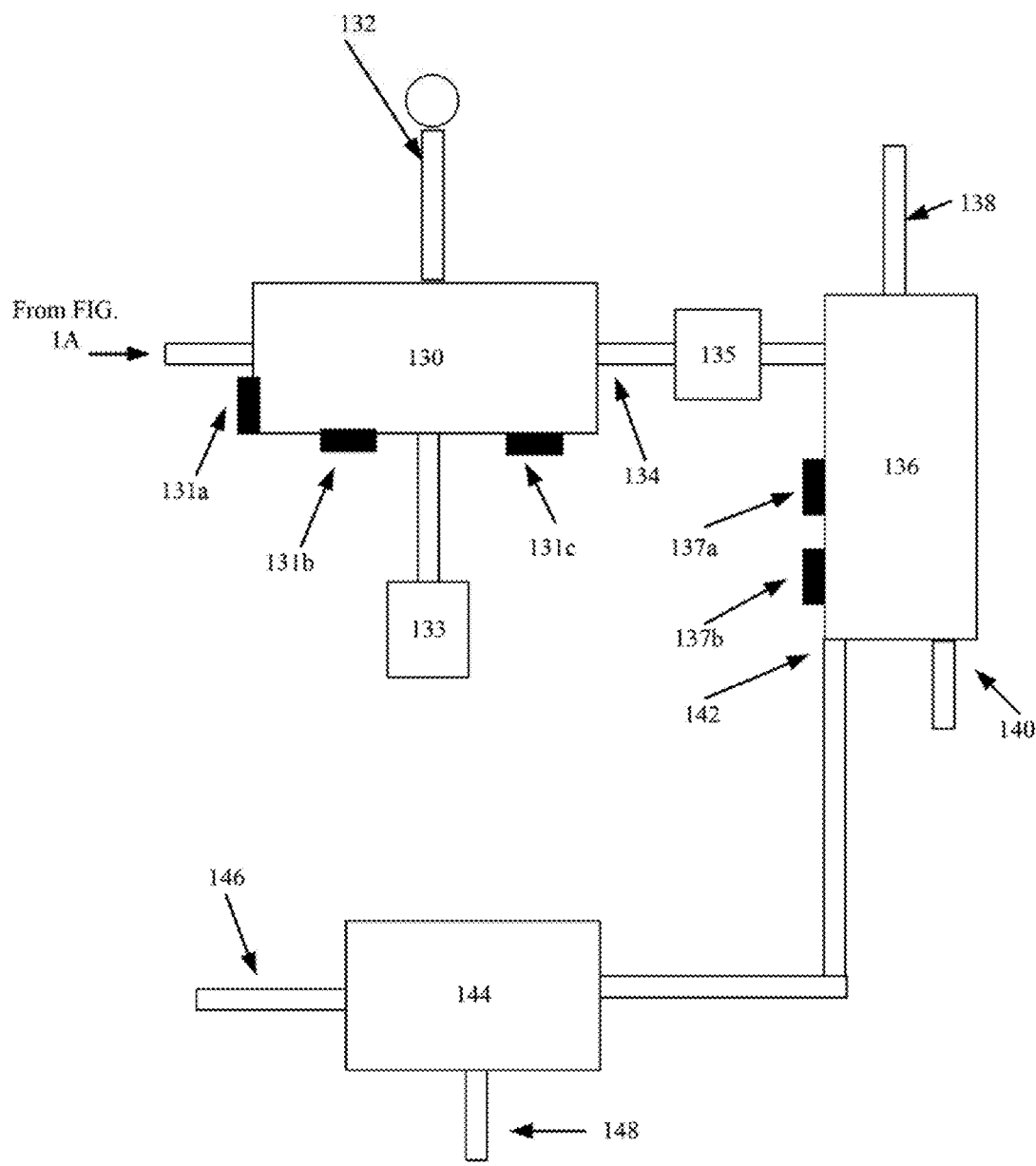

FIGS. 1A and 1B illustrate an embodiment of a system that may be used for generating power from $H_2O$, $CO_2$, $O_2$, and a carbon feedstock. Improved efficiency may be obtained in part by having the fuel generating facility also produce at least some electric power to lessen the facility's dependence on exterior power supplies. Improved efficiency may also be obtained by a facility having multiple points of process control to properly adjust reaction temperatures and other process conditions to optimize the processes.

Within a first processing chamber 100, a first fluid plasma, a second fluid plasma, and a third fluid plasma may be introduced. The first fluid plasma may be generated by exposing a first working fluid to a first high voltage electric field, such as may be generated by a first plasma torch 102a, the second fluid plasma may be generated by exposing a second working fluid to a second high voltage electric field, such as may be generated by a second plasma torch 102b, and the third fluid plasma may be generated by exposing a third working fluid to a third high voltage electric field, such as may be generated by a third plasma torch 102c. In some embodiments, the first working fluid may be carbon dioxide gas ($CO_2$), the second working fluid may be oxygen gas ($O_2$), and the third working fluid may be water vapor ($H_2O$). In some embodiments, the first fluid plasma, second fluid plasma, and third fluid plasma may each attain a temperature of about 20,000 degrees C. at the output of their respective plasma torches (102a, 102b, and 102c).

Figure 1C:
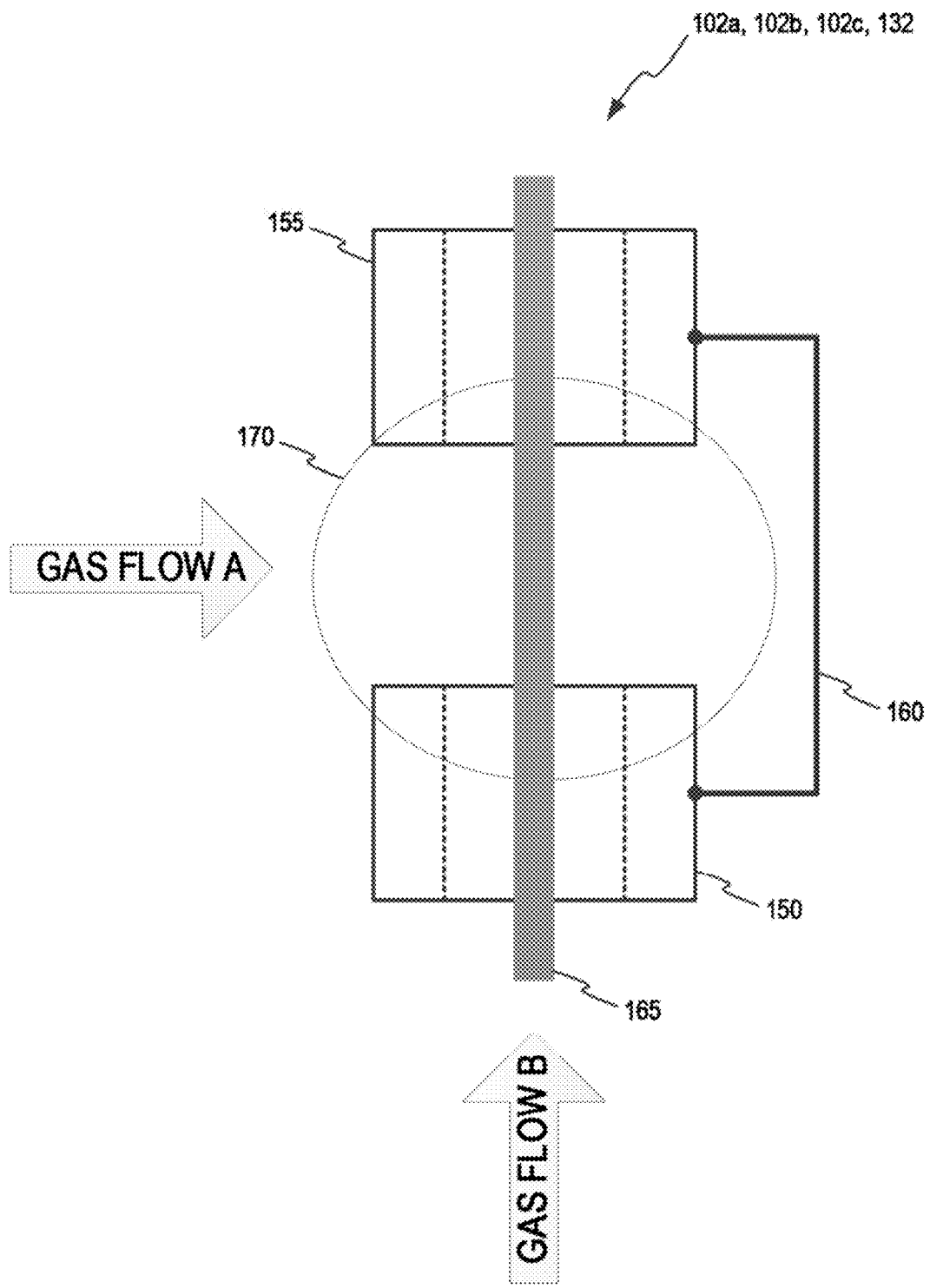
FIG. 1C depicts a block diagram of an illustrative high-voltage electric field generator according to an embodiment.

Each of the one or more high-voltage electric field generators 102a, 102b, 102c, 132 may generally be any of various components that may be used to generate a high voltage potential. Thus, as shown in FIG. 1C, each of the one or more high-voltage electric field generators 102a, 102b, 102c, 132 may have at least one anode surface 150, at least one cathode surface 155, and an electric potential 160 between the anode surface and the cathode surface. As a result, a magnetic field 165 and an electric field 170 may be generated when the electric potential 160 is applied between the at least one anode surface 150 and the at least one cathode surface 155. In some embodiments, a flow of gas, as described in greater detail herein and indicated by the horizontal arrow, may be substantially perpendicular to the magnetic field 165. In other embodiments, the flow of gas, as indicated by the vertical arrow, may be substantially parallel to the magnetic field 165. The magnetic field 165 and the electric field 170 may each have an effect on gas that flows through a gap between the anode surface 150 and the cathode surface 155. In a non-limiting example, the electric field 170 may stabilize the gas and/or ionize the gas. In another non-limiting example, the magnetic field 165 may alter a spin and/or a velocity of the gas.

It may be appreciated that the $CO_2$, $O_2$, and $H_2O$ in the first processing chamber 100 may be used as working fluids for their respective plasma torches (102a, 102b, and 102c). Thus, each gas may be exposed to high voltage electric fields. As a result of exposure to such fields, the gases may be reduced to free radical species (as examples, for $H_2O$, these may include the hydroxyl radical OH., and for $O_2$ these may include the superoxide anion radical $O2.^-$) in addition to ionized species (for $O_2$, these may include $O^-$, $O_2^-$, $O_2^+$, and $O^+$). The types and amounts of reactive species created by exposure of the gases to high voltage electric fields may differ from those generated by exposure of the gases to heat alone.

In one non-limiting example of the method, exposing the first working fluid to a first high voltage electric field may include providing an anode surface and a cathode surface separated by a distance to create a gap between the two surfaces. A first high voltage electric potential may be induced between the anode surface and the cathode surface, and the first working fluid may be induced to traverse the gap between the two surfaces. The gap may generally be selected such that (for the electrical voltage selected), the electrical field is about 0.3 kV/cm to about 8.0 kV/cm, including about 0.3 kV/cm, about 0.3149 kV/com, about 0.5 kV/cm, about 0.75 kV/com, about 1.0 kV/com, about 1.25 kV/cm, about 1.5 kV/cm, about 1.574 kV/cm, about 2.0 kV/com, about 2.5 kV/cm, about 3.0 kV/cm, about 0.3149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided between the anode surface and the cathode surface. For example, a first high voltage electric potential may be induced between the anode surface and the cathode surface, and the first working fluid may be induced to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

In another non-limiting example of the method, exposing the second working fluid to a second high voltage electric field may include providing an anode surface and a cathode surface separated by a distance to create a gap between the two surfaces. A second high voltage electric potential may be induced between the anode surface and the cathode surface, and the second working fluid may be induced to traverse the gap between the two surfaces. The gap may generally be selected such that (for the electrical voltage selected), the electrical field is about 0.3 kV/cm to about 8.0 kV/cm, including about 0.3 kV/cm, about 0.3149 kV/com, about 0.5 kV/cm, about 0.75 kV/com, about 1.0 kV/com, about 1.25 kV/cm, about 1.5 kV/cm, about 1.574 kV/cm, about 2.0 kV/com, about 2.5 kV/cm, about 3.0 kV/cm, about 0.3149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided between the anode surface and the cathode surface. For example, a second high voltage electric potential may be induced between the anode surface and the cathode surface, and the second working fluid may be induced to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

In another non-limiting example of the method, exposing the third working fluid to a third high voltage electric field may include providing an anode surface and a cathode surface separated by a distance to create a gap between the two surfaces. A third high voltage electric potential may be induced between the anode surface and the cathode surface, and the third working fluid may be induced to traverse the gap between the two surfaces. The gap may generally be selected such that (for the electrical voltage selected), the electrical field is about 0.3 kV/cm to about 8.0 kV/cm, including about 0.3 kV/cm, about 0.3149 kV/com, about 0.5 kV/cm, about 0.75 kV/com, about 1.0 kV/com, about 1.25 kV/cm, about 1.5 kV/cm, about 1.574 kV/cm, about 2.0 kV/com, about 2.5 kV/cm, about 3.0 kV/cm, about 0.3149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided between the anode surface and the cathode surface. For example, a third high voltage electric potential may be induced between the anode surface and the cathode surface, and the third working fluid may be induced to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

It may be understood that the anode and cathode surfaces contacting the first working fluid, the second working fluid, and the third working fluid may be the same set of surfaces or they may differ. If each working fluid contacts an independent pair of anode and cathode surfaces, the respective gap distances may be essentially the same or different, and high voltage electric potentials to which the working fluids are exposed may have essentially the same or different characteristics.

It may be appreciated that each source of the high voltage electric field, such as those exemplified by plasma torches $102a$, $102b$, and $102c$, may be controlled by one or more control systems. Such control systems may be specific for all the plasma torches $102a$, $102b$, and $102c$ together and may be different from or included with a control system for the entire power generating system. Alternatively, each plasma torch $102a$, $102b$, and $102c$, may have a separate control system. A control system for a plasma torch $102a$, $102b$, and $102c$, may include control functions for torch parameters, such as, but not limited to, the voltage of the high voltage electric field and a frequency of the high voltage electric field. Control of the torches $102a$, $102b$, and $102c$, may be based on one or more process measurements, including but not limited to, a measurement of a voltage applied to components that may generate the high voltage electric field, a current drain of a voltage supply for the high voltage electric field generators (such as plasma torches $102a$, $102b$, and $102c$), the temperature of the plasma output of the high voltage electric field generators (provided by a temperature sensor $101a$), and the composition of the plasma generated by the high voltage electric field generators (provided by a gas composition sensor $101b$). It may further be appreciated that each of the high voltage electric field generators (as exemplified by plasma torches $102a$, $102b$, and $102c$) may be controlled according to one or more process algorithms. The plasma torches $102a$, $102b$, and $102c$ may be controlled according to the same process methods or algorithms (as provided by individual controllers or a single controller). Alternatively, each of the plasma torches $102a$, $102b$, and $102c$ may be controlled according to a different process method or algorithm (as provided by individual controllers or by a single controller).

Each working fluid may be supplied by its own working fluid source. In one non-limiting example, $CO_2$ may be supplied from a $CO_2$ source $104$, $O_2$ may be supplied from an $O_2$ source $106$, and water vapor ($H_2O$) may be supplied from an $H_2O$ source $108$. It may be recognized that control of the fluid plasma from each of the high voltage field sources may also include control the amount of working fluid supplied to each of the high voltage field sources. Although not shown, it is apparent that the working fluid supply sources for the $CO_2$, $O_2$, and $H_2O$, ($104$, $106$, and $108$, respectively) may also include control and measurement components. Such components may include, without limitation, components to control the amount of the working fluid supplied by each of the working fluid supply sources (valves) and devices to measure the amount of each of the working fluid supplied (as non-limiting examples, by measuring chemical composition or pressure of the gas delivered). It may be further understood that such measurement and control devices may be controlled by one or more control systems, as disclosed above. Such control systems may be specific to one or more of the working fluid supply sources. Alternatively, all the working fluid supply sources may be controlled by the same control system. In an alternative embodiments, the working fluid supply sources may be controlled by a control system common to the entire power generation system.

Although not illustrated in FIG. 1, an alternative embodiment of the system may include three working fluids, exemplified by $CO_2$, $O_2$ and $H_2O$, that may be combined into one or two combined working fluids before being supplied to one or two high voltage electric field generators. As a non-limiting example, $CO_2$, $O_2$ and $H_2O$ may be combined into a single combined working fluid to be supplied to a single plasma torch. By extension, the controllers associated with each of the supply sources for the $CO_2$, $O_2$ and $H_2O$, ($104$, $106$, and $108$, respectively) may cause a specific amount of each gas to be added to the combined working fluid to produce an optimized ratio of gasses. Similarly, the controller associated with a single plasma torch may cause the plasma torch to operate under optimum conditions for a specific ratio of gasses in the combined working fluid.

The first fluid plasma, the second fluid plasma, and the third fluid plasma together may be directed to contact a carbon-based feed-stock within the first processing chamber, thereby creating a first fluid mixture. The carbon-based feed-stock may be supplied from a carbon-based feed-stock supply $110$. The mechanical components used to transport the carbon-based feed-stock into the first processing chamber $100$ may be controlled according to some process parameters. The control of the transport of the carbon-based feed-stock may be supplied by a control system. Such a control system may be specific to the mechanical components used to transport the carbon-based feed-stock into the first processing chamber $100$. Alternatively, such a control system may be included into a control system to control the entire power generation system. Without limitation, examples of the carbon-based feed-stock may include one or more of organic waste (wood chips, sawdust, material made from organic material such as papers, wood furniture), municipal waste, man-made organic material (synthetic carpets, tires, compact discs, plastics, rubbers), coal, and biomass.

In some non-limiting examples, the first processing chamber 100 may also be maintained at a vacuum. In one non-limiting example, vacuum may be provided by means of a vacuum pump equivalent device 111. In one non-limiting example, the first process chamber 100 may be maintained at a pressure of about 50 kPa (0.5 atmospheres). The pressure within the first processing chamber 100 may be monitored by a pressure sensor 101c.

The first fluid mixture, while in the first processing chamber 100, may attain temperatures of about 4000 degrees C. to about 6000 degrees C. Higher or lower temperatures may be attained according to the conditions under which the high voltage field generators operate. The first fluid mixture may be cooled within the first processing chamber 100, at an exit port of the first processing chamber 112, in a transport device (such as a pipe or other duct-work) at an exit of the first processing chamber, or at a combination of these locations through the action of a coolant addition device 114. In one non-limiting example, the coolant may include liquid oxygen (LOX). An amount of coolant introduced into the first fluid mixture by the coolant addition device 114 may be controlled by a control system. In some non-limiting examples, the amount of the coolant added to the first fluid mixture may be controlled according to a temperature of the first fluid mixture, a composition of the first fluid mixture, or other measured parameters of the first fluid mixture. Such a control system may be associated only with the coolant addition device 114. Alternatively, such a control system may be incorporated into a system for controlling the entire power generation system. The addition of the coolant to the first fluid mixture may reduce the temperature of the resulting fluid mixture (an admixed first fluid mixture) to about 1450 degrees C. to about 1650 degrees C. It may be further appreciated that the admixed first fluid mixture may have a composition different from that of the first fluid mixture.

The admixed first fluid mixture may be transported to a first heat exchange device 118 where it may exchange at least some of its heat with a heat exchange material, and thus cool to form a second fluid mixture. In some non-limiting examples, the first heat exchange device 118 may be a first heat recovery steam generator (HRSG). The first heat exchange device 118 may allow transfer of at least some heat from the admixed first fluid mixture to a heat exchange material, such as water. Water may enter the first heat exchange device 118 through a first water input port 120, and the amount of water may be controlled by a control system. The heated first heat exchange material, which may include steam as a non-limiting example, may exit the first heat exchange device 118 by means of a first output port 122. The heated first heat exchange material may be further transported to a first electric turbine to generate a first supply of electric power.

In one non-limiting example, the first heat exchange material may be water, which may be converted to a first supply of steam in the first heat exchange device 118. Once the first supply of steam has activated the electric turbine, the first supply of steam may be cooled to liquid water. In some embodiments, the liquid water may be returned to the first heat exchange device 118 to be reheated by more of the admixed first fluid mixture. Alternatively, the first supply of steam, after activating the first electric turbine, may be returned to a working fluid source 108 to be supplied to a high voltage electric field generator (such as plasma torch 102c).

At an output port 126 of the first heat exchange device 118, the second fluid mixture may have a temperature of about 38 degrees C. to about 200 degrees C. The temperature within the first heat exchange device 118 may be monitored by a temperature sensor 119a. The composition of the second fluid mixture may be different from that of the first fluid mixture and that of the admixed first fluid mixture. The composition of the second fluid mixture may be monitored within or at the exit of the first heat exchange device 118 by means of a composition sensor 119b. The components of the second fluid mixture may be separated by a gas separator 128 and the individual components may be directed to individual gas holding containers 129a, 129b.

The individual components may include one or more of hydrogen gas ($H_2$), and carbon monoxide (CO). The gas separator may comprise, as non-limiting examples, a membrane separation system, a molecular sieve, or a combination thereof. The individual gas holding containers 129a, 129b, for example an $H_2$ container and a CO container, may each include an outflow metering device. Each outflow metering device may be controlled by a controller. Alternatively, the outflow metering devices of each of the gas holding containers 129a, 129b may be controlled by the same controller. Each gas holding container 129a, 129b may also have a gas output port associated with the corresponding outflow metering devices. The gas output port of each of the gas holding containers 129a, 129b may direct the gas from its gas holding container into a common supply duct 132. Some portion of the second fluid mixture may also be directed into the common supply duct 132.

The outflow metering devices of each of the gas holding containers 129a, 129b may be controlled to permit an amount of gas into the common supply duct 132 to create a syngas mixture having a controlled composition. In one non-limiting example, the syngas mixture composition may be controlled based on one or more gas composition sensors 133 associated with the common supply duct 132. In another non-limiting example, the syngas mixture composition may be controlled based on a volume of gas emitted by the outflow metering devices of each of the individual gas holding containers 129a, 129b. In yet another non-limiting example, the syngas mixture composition may be controlled based on the pressure of gas contained in each of the gas holding containers 129a, 129b. In some embodiments, a composition of the syngas may include 1 part CO to 2 parts $H_2$ (1:2). In other embodiments, the ratio of CO to $H_2$ in the syngas may be from about 1:1.2 to about 1:3.

The syngas mixture may be directed by the common supply duct 132 into a second processing chamber 130. The syngas may be heated by one or more high voltage electrical field generator 132. The plasma may attain a temperature of about 20,000 degrees C. at the output of additional high voltage electrical field generators 132, and the second processing chamber 130 may attain temperatures of about 4000 degrees C. to about 6000 degrees C. As a result of the second heating in the second processing chamber 130, a third fluid mixture may be obtained from the syngas. The second processing chamber 130 may be maintained at a pressure (greater than, equal to, or less than atmospheric pressure) by means of a vacuum pump 133 or similar device. Process control variables within the second processing chamber 130 may be monitored by any number of sensors including, but not limited to, a temperature sensor 131a, a gas composition sensor 131b, or a pressure sensor 131c.

The third fluid mixture may be cooled within the second processing chamber 130, at an exit port of the first processing chamber 134, in a transport device (such as a pipe or other duct-work) at an exit of the first processing chamber, or at a combination of these locations through the action of a second coolant addition device 135. In one non-limiting example, the coolant may include liquid oxygen (LOX). An amount of coolant introduced into the third fluid mixture by the second coolant addition device 135 may be controlled by a control system. In some non-limiting examples, the amount of the coolant added to the third fluid mixture may be controlled according to a temperature of the third fluid mixture, a composition of the third fluid mixture, or other measured parameters of the third fluid mixture. Such a control system may be associated only with the second coolant addition device. Alternatively, such a control system may be incorporated into a system for controlling the entire power generation system. The addition of the second coolant to the third fluid mixture may reduce the temperature of the resulting fluid mixture (an admixed third fluid mixture) to about 1450 degrees C. to about 1650 degrees C.

The heated admixed third fluid mixture may be transported to a second heat exchange device 136 where it may exchange at least some of its heat with a heat exchange material, and thus cool to form an effluent mixture. In some non-limiting examples, the second heat exchange device 136 may be a second heat recovery steam generator (HRSG). The second heat exchange device 136 may allow transfer of at least some heat from the third admixed fluid mixture to a second heat exchange material, such as water. Water may enter the second heat exchange device 136 through a second water input port 138 and the amount of water may be controlled by a control system. The heated second heat exchange material, which may include steam as a non-limiting example, may exit the second heat exchange device 136 by means of a second output port 140. The heated second heat exchange material may be further transported to a second electric turbine to generate a second supply of electric power.

In one non-limiting example, the second heat exchange material may be water, which may be converted to a second supply of steam in the second heat exchange device 136. Once the second supply of steam has activated the electric turbine, the second supply of steam may be cooled to liquid water. In some embodiments, the liquid water may be returned to the second heat exchange device 136 to be reheated by more of the third fluid mixture. Alternatively, the second supply of steam, after activating the second electric turbine, may be returned to a working fluid source 108 to be supplied to a high voltage electric field generator (such as plasma torch 102*c*).

It may be appreciated that the temperature of the admixed first fluid entering the first heat exchange device 118 may be different than the temperature of the heated admixed third fluid entering the second heat exchange device 136. As a result, the power derived from the heated first heat exchange material through the first electric turbine may be different from that derived from the heated second heat exchange material through the second electric turbine. In some non-limiting examples, process parameters in the second heat exchange device 136 may be monitored by a temperature 137*a* and a gas composition sensor 137*b*.

In one non-limiting embodiment, the second electric turbine may be the same as the first electric turbine.

The effluent fluid from the second heat exchange device 136 may be directed via an output port 142 to any number of cleaning devices 144 to remove unwanted components, non-limiting examples being sulfur-containing material and mercury-containing materials. Examples of such cleaning devices 144 may include, without limitation, a wet limestone scrubber.

The resultant gas mixture exiting the cleaning devices 144 may include primarily carbon dioxide $CO_2$ and water $H_2O$. In some embodiments, such gases may be released into the atmosphere. In other embodiments, the gases may be returned to be re-used at appropriate points in the process. For example, the $CO_2$ may be returned to the $CO_2$ supply source 104 through a $CO_2$ output port 146, while the water may be returned to the water supply source 108 for re-used in the first processing chamber 100 through a water supply output port 148.

It may be appreciated that the system disclosed above may make use of data derived from a number of sensors of processor parameters associated with a variety of stages including, without limitation, the first processing chamber 100, the second processing chamber 130, the first heat exchange device 118, the second heat exchange device 136 and the common supply duct 132. Data from the sensors may be used by one or more control systems used to control any one or more devices including the one or more high voltage electric field generators (102*a*, 102*b*, 102*c*, 132), vacuum pumps (111, 133), suppliers of working gases to the electric field generators (102*a*, 102*b*, 102*c*, 132), and similar devices.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity. It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method of producing electrical power, the method comprising:
   providing a first processing chamber;
   providing a first working fluid;
   exposing the first working fluid to a first high voltage electric field to produce a first fluid plasma, wherein the first fluid plasma is contained in the first processing chamber;
   providing a second working fluid;
   exposing the second working fluid to a second high voltage electric field to produce a second fluid plasma, wherein the second fluid plasma is contained in the first processing chamber;
   providing a third working fluid;
   exposing the third working fluid to a third high voltage electric field to produce a third fluid plasma, wherein the third fluid plasma is contained in the first processing chamber;
   providing a carbon-based feed-stock;
   contacting the carbon-based feed-stock with the third fluid plasma, the second fluid plasma, and the first fluid plasma to form a first fluid mixture within the first processing chamber;
   adding a coolant to the first fluid mixture, thereby forming an admixed first fluid mixture;
   contacting the admixed first fluid mixture with a first heat exchange device to form a second fluid mixture and to heat a first heat exchange material;
   transporting the heated first heat exchange material to a first electric turbine to generate a first supply of electric power;
   separating the components of the second fluid mixture and storing at least one of the components;
   combining one or more of the components of the second fluid mixture thereby forming a syngas;
   heating the syngas within a second processing chamber to form a heated third fluid mixture;
   adding a coolant to the heated third fluid mixture, thereby forming an admixed third fluid mixture;
   contacting the admixed third fluid mixture with a second heat exchange device to form an effluent mixture and to heat a second heat exchange material;
   contacting the heated second heat exchange material with a second electric turbine to generate a second supply of electric power; and
   contacting the effluent mixture to a wet scrubber.

2. The method of claim 1, wherein the first working fluid is oxygen gas.

3. The method of claim 1, wherein the second working fluid is water vapor.

4. The method of claim 1, wherein the third working fluid is carbon dioxide gas.

5. The method of claim 1, wherein exposing the first working fluid to a first high voltage electric field comprises:
   providing an anode surface;
   providing a cathode surface at a distance from the anode surface to create a gap between the anode surface and the cathode surface;
   providing a first high voltage electric potential between the anode surface and the cathode surface of about 2.4 kV times the distance in centimeters to about 60 kV times the distance in centimeters; and
   causing the first working fluid to traverse the gap.

6. The method of claim 1, wherein exposing the second working fluid to a second high voltage electric field comprises:
   providing an anode surface;
   providing a cathode surface at a distance from the anode surface to create a gap between the anode surface and the cathode surface;
   providing a second high voltage electric potential between the anode surface and the cathode surface of about 2.4 kV times the distance in centimeters to about 60 kV times the distance in centimeters; and
   causing the second working fluid to traverse the gap.

7. The method of claim 1, wherein exposing the third working fluid to a third high voltage electric field comprises:
   providing an anode surface;

providing a cathode surface at a distance from the anode surface to create a gap between the anode surface and the cathode surface;

providing a third high voltage electric potential between the anode surface and the cathode surface of about 2.4 kV times the distance in centimeters to about 60 kV times the distance in centimeters; and causing the third working fluid to traverse the gap.

8. The method of claim 1, wherein exposing the first working fluid to a first high voltage electric field comprises causing the first working fluid to pass through a first plasma torch, wherein exposing the second working fluid to a second high voltage electric field comprises causing the second working fluid to pass through a second plasma torch, and wherein exposing the third working fluid to a third high voltage electric field comprises causing the third working fluid to pass through a third plasma torch.

9. The method of claim 1, wherein exposing the first working fluid to a first high voltage electric field comprises causing the first working fluid to pass through a plasma torch, wherein exposing the second working fluid to a second high voltage electric field comprises causing the second working fluid to pass through the plasma torch, and wherein exposing the third working fluid to a third high voltage electric field comprises causing the third working fluid to pass through the plasma torch.

10. The method of claim 1, wherein the carbon-based feed stock comprises one or more of the following: coal and biomass.

11. The method of claim 1, wherein the first fluid mixture has a temperature of about 7230° F. (4000° C.) to about 36000° F. (20000° C.).

12. The method of claim 1, wherein the syngas comprises at least carbon monoxide and hydrogen gas.

13. The method of claim 1, wherein the first heat exchange device is a first heat recovery steam generator.

14. The method of claim 1, wherein the heated second fluid mixture has a temperature of about 2950° F. (1620° C.) to about 4000° F. (2200° C.).

15. The method of claim 1, wherein the second electric turbine is the same as the first electric turbine.

16. The method of claim 5, wherein the first high voltage electric potential has a frequency of about 1 MHz to about 50 MHz.

17. The method of claim 6, wherein the second high voltage electric potential has a frequency of about 1 MHz to about 50 MHz.

18. The method of claim 7, wherein the third high voltage electric potential has a frequency of about 1 MHz to about 50 MHz.

19. The method of claim 12, wherein the syngas comprises at least carbon monoxide and hydrogen gas in a ratio of about 1:2.

20. The method of claim 13, wherein the second working fluid comprises at least in part an amount of steam generated by the heat recovery steam generator.

* * * * *